(12) United States Patent
Banks

(10) Patent No.: US 7,382,944 B1
(45) Date of Patent: Jun. 3, 2008

(54) PROTECTIVE COATING AND HYPERTHERMAL ATOMIC OXYGEN TEXTURING OF OPTICAL FIBERS USED FOR BLOOD GLUCOSE MONITORING

(75) Inventor: Bruce A. Banks, Olmstead Township, OH (US)

(73) Assignee: The United States of America as represented by the Administration of the National Aeronautics and Space Administration, Washington, DC (US)

( * ) Notice: Subject to any disclaimer, the term of this patent is extended or adjusted under 35 U.S.C. 154(b) by 195 days.

(21) Appl. No.: 11/489,813

(22) Filed: Jul. 14, 2006

(51) Int. Cl.
G02B 6/00 (2006.01)
G02B 6/34 (2006.01)
G02B 6/26 (2006.01)
G02B 6/42 (2006.01)

(52) U.S. Cl. .............................. 385/12; 385/37; 385/38

(58) Field of Classification Search .................. 385/12, 385/37, 38
See application file for complete search history.

(56) References Cited

U.S. PATENT DOCUMENTS

| | | | |
|---|---|---|---|
| 4,788,082 A | 11/1988 | Schmitt | |
| 4,874,222 A | 10/1989 | Vacha et al. | |
| 5,026,135 A | 6/1991 | Booth | |
| 5,246,746 A | 9/1993 | Michalske et al. | |
| 5,320,814 A | 6/1994 | Walt et al. | |
| 5,378,628 A | 1/1995 | Gratzel et al. | |
| 5,415,946 A | 5/1995 | Friz | |
| 5,534,314 A | 7/1996 | Wadley et al. | |
| 5,560,781 A * | 10/1996 | Banks et al. .................... | 134/1 |
| 5,858,456 A | 1/1999 | Nordlander | |
| 5,859,937 A | 1/1999 | Nomura | |
| 6,200,737 B1 | 3/2001 | Walt | |
| 6,210,910 B1 | 4/2001 | Walt et al. | |
| 6,331,438 B1 | 12/2001 | Aylott et al. | |
| 6,576,101 B1 | 6/2003 | Heller et al. | |
| 6,602,702 B1 | 8/2003 | McDevitt et al. | |
| 6,638,772 B1 | 10/2003 | Douglas et al. | |
| 6,667,159 B1 | 12/2003 | Walt et al. | |
| 7,305,154 B1 * | 12/2007 | Banks .......................... | 385/12 |
| 7,308,164 B1 * | 12/2007 | Banks .......................... | 385/12 |

(Continued)

FOREIGN PATENT DOCUMENTS

JP 2001305398 10/2001

(Continued)

Primary Examiner—M. R. Connelly-Cushwa
Assistant Examiner—Rhonda S Peace
(74) Attorney, Agent, or Firm—Gary Borda; Robert Rotella

(57) ABSTRACT

Disclosed is a method of producing cones and pillars on polymethylmethacralate (PMMA) optical fibers for glucose monitoring. The method, in one embodiment, consists of using electron beam evaporation to deposit a non-contiguous thin film of aluminum on the distal ends of the PMMA fibers. The partial coverage of aluminum on the fibers is randomly, but rather uniformly distributed across the end of the optical fibers. After the aluminum deposition, the ends of the fibers are then exposed to hyperthermal atomic oxygen, which oxidizes the areas that are not protected by aluminum. The resulting PMMA fibers have a greatly increased surface area and the cones or pillars are sufficiently close together that the cellular components in blood are excluded from passing into the valleys between the cones and pillars. The optical fibers are then coated with appropriated surface chemistry so that they can optically sense the glucose level in the blood sample than that with conventional glucose monitoring.

27 Claims, 7 Drawing Sheets

U.S. PATENT DOCUMENTS

| | | |
|---|---|---|
| 2002/0051613 A1 | 5/2002 | Singh |
| 2002/0068167 A1 | 6/2002 | Veerasamy |
| 2003/0032204 A1 | 2/2003 | Walt et al. |
| 2003/0077205 A1 | 4/2003 | Xu |
| 2003/0148401 A1* | 8/2003 | Agrawal et al. ............. 435/7.9 |
| 2005/0123451 A1 | 6/2005 | Nomura |

FOREIGN PATENT DOCUMENTS

| | | |
|---|---|---|
| JP | 2004212711 A | 7/2004 |
| JP | 2005029856 A | 2/2005 |
| WO | WO 98145688 | 10/1998 |

* cited by examiner

PROTECTIVE COATING AND HYPERTHERMAL ATOMIC OXYGEN TEXTURING OF OPTICAL FIBERS USED FOR BLOOD GLUCOSE MONITORING

ORIGIN OF THE INVENTION

The invention described herein was made by an employee of the United States Government and may be used by or for the Government for governmental purposes without payment of any royalties thereon or therefor.

CROSS REFERENCE TO RELATED APPLICATIONS

This application is related to U.S. patent application Ser. No. 10/942,637 filed Sep. 16, 2004.

FIELD OF THE INVENTION

The present invention relates to a sensing device for determination of compounds in fluids, and more particularly, to a single solid light-conducting fiber comprising the sensing device with a point of attachment and having a textured surface consisting of a distal end having a non-contiguous protective coating deposited thereon and being relatively uniformly distributed across the textured surface. The protective coating is then being further treated by being placed in a vacuum system and then subjected to directed hyperthermal beams comprising oxygen ions or atoms.

BACKGROUND OF THE INVENTION

The quantification of chemical and biochemical components in aqueous fluids, and particularly in biological fluids, such as whole blood or urine and in biological fluid derivatives such as serum and plasma, is of ever increasing importance. Important applications exist in medical diagnosis and treatment and in the quantification of exposure to therapeutic drugs, intoxicants, hazardous chemicals and the like. These applications include the detection and quantification of an increasing variety of certain circulating antibodies, cancer-related metabolites, genetically derived chemical tracers, and hormones emitted during events such as pregnancy. In many instances, the amounts of materials being determined are minuscule in the range of a microgram or less per deciliter.

One common medical test is the measurement of blood glucose levels by diabetics which is more fully described in U.S. Pat. No. 5,859,937 ('937) of H. Nomura and herein incorporated by reference. Portions of the teachings of the '937 patent are used herein for the sake of completeness. The glucose determination, as described in the '937 patent, typically entails the diabetic piercing the skin of his or her finger with a lance, followed by squeezing or expression of a blood droplet. The blood droplet is then transferred to a reagent pad or test strip. The amount of blood that is conveniently expressed from a finger prick is governed by the size and depth of penetration of the lance. Too small a nick results in an inadequately sized blood sample for the intended analysis. Conversely, too deep a nick results in an oversized blood sample. Pain is experienced in the lancing procedure, and the degree of pain is associated with the size and depth of penetration of the lance.

The teachings of the '937 patent provides a textured site allowing for an increased surface area compared to other prior art devices, for use in blood sampling. The increased surface area provides an advantage relating to minimizing the invasive feature of glucose testing because the surface area being very small, greatly reduces the level of analyte-responsive needed to be deposited to perform the glucose determination. Increased surface area allows one to utilize a small blood droplet, for instance, a droplet having a volume of one (1) to five (5) microliters, or preferably 1 to 2.5 microliters. The '937 patent allows for a reduction relative to the prior art thereof, of about one-fifth to about one-tenth of the fluid volume necessary blood glucose sensing. It is desired that further improvements to the surface area be provided, so as to correspondingly reduce the amount of blood necessary for determination of glucose for diabetics.

The '937 patent provides a textured surface using various means, such as ion beam sputtering, plasma etching including atomic oxygen plasma, physical abrasion, chemical etching, sputtering or ablation by high energy beams, or deposition of dendritic-like structures thereon. The textured surface of the '937 patent is intended to provide a means for separating cellular components in blood from the plasma of the blood so as to allow optical sensing of the glucose concentration in the blood. The processes described in the '937 patent for developing the textured surface need to produce a cone or pillar structure at the ends of optical fibers or other sensing surfaces which are sufficiently close—so as to prevent the cellular components from entering the microscopic valleys between the cones or pillars so that optical sensing of the glucose concentration can be performed. Also, it is desired to have a sufficiently high aspect ratio (height to width) of cones or pillars to allow sufficient surface area for optical determination of the glucose concentration in the blood.

In pursuit for finding desired pillar structures for the textured surfaces, some of the different processes mentioned in the '937 patent were investigated and may be further described with reference to FIG. 1 herein, which illustrates a Scanning Electron Microscope image of the end of a polymethylmethacrylate optical fiber that was textured by the use of thermal energy (<0.5 eV) atomic oxygen through salt dust for enhancing texturing.

The disadvantages of prior art results shown in FIG. 1 is that the craters produced were too wide to prevent cellular blood components from entering the optical sensing areas and the aspect ratio (height to width) of the surface features does not offer high gains in surface area relative to flat surfaces. As can be seen in FIG. 1, the cone or crater ridges are approximately 20-30 microns apart far too much to achieve their desired goals. More particularly, the spacing between cones or ridges needs to be ≦5 microns to block the entry of blood cells into the cone valleys. Thus, the craters did not provide separation of the plasma from the blood in the areas of the valleys between the cones or pillars where optical sensing of the glucose concentration needs to occur. Use of thermal energy (<0.5 eV) atomic oxygen, sometimes referred to as isotropic thermal energy, to texture the surfaces of clear polymers such as polymethylmethacrylate, polystyrene or other hydrocarbon polymer (even with the use of small particle salt shielding) causes wide almost hemispherical craters to form surface features which are only as high as they are wide. The aspect ratio of only approximately one (1) requires greater volume blood samples than desirable. It is desired that textured surfaces for optical sensors used for blood testing be provided that provide cones or pillars that are spaced apart from each other by less than 5 microns, preferably about 1 micron, and having an aspect ratio (height to width) of greater than one (1).

The previously mentioned related U.S. patent application Ser. No. 10/942,637 filed Sep. 16, 2004 describes a process for providing optical sensors having the desired spacing between cones or pillars of less than 5 microns and an aspect ratio of greater than one. Although U.S. patent application Ser. No. 10/942,637 achieves its desired goals, it is further desired that an additional process be provided that produces optical sensors having a textured surface comprising cones or pillars that are spaced apart from each other by less than five (5) microns, preferably about 1 micron, and have an aspect ratio of greater than one (1) micron.

Another process related to optical fibers is disclosed in U.S. Pat. No. 6,200,737B1 ('737B1) of Walt et al that employs photolithograph. The cost of using photolithography on the ends of multiple bundle fibers is exceedingly high for blood glucose monitoring because it is extremely difficult to simply stack a half million of the multiple bundle fibers together to be used for blood glucose monitoring and perform photolithography thereon as disclosed in the '737B1 patent. More particularly, because of the small size and the requirement that only short (1-2 cm) lengths need to be used for blood glucose monitoring, it would require the half million stacking. This stacking can be simplified however, as contemplated by the practice of the present invention, by using large single fibers where no individual surface treatment need be applied. Thus, the cost of the complex process of the '737 patent to place surface texture on the associated fibers is unnecessarily and disadvantageously high.

OBJECTS OF THE INVENTION

It is a primary object of the present invention to provide a process that creates a sensor having a textured surface comprising cones or pillars that are spaced apart from each other by less than 5 microns, preferably about 1 micron, and having an aspect ratio of greater than one (1).

Moreover, it is an object of the present invention to provide a process for making fine texture, high aspect ratio come surface at the distal end of a solid light-conducting fiber that is necessary for optical fiber blood glucose monitoring with small blood samples.

It is a further object of the present invention to provide for an optical sensor having cones or pillars that are sufficiently close so as to prevent cellular blood components for interfering with optical sensing of the blood glucose concentration.

Still further, it is an object of the present invention to provide a process that creates a textured surface for an optical sensing device which has a high surface area that correspondingly allows for a reduction in the amount of blood needed to be removed from a patient so as to reduce the pain to which the patient needs to be subject for glucose determination.

It is a further object of the present invention to provide for optical polymer devices serving the sensors that may be used for blood plasma diagnostics that require economic separation of plasma in the whole blood for optical sensing measurements.

Further still, it is an object to provide optical fibers used for blood glucose monitoring without suffering the drawbacks of photolithographical processes.

In addition, it is an object of the present invention to provide optical fibers having diameters so as to be sufficiently sturdy to be conveniently used for blood glucose monitoring.

Further, it is an object of the present invention to provide optical fibers having textured surface with desired shapes so as to be advantageously used in blood glucose monitoring.

SUMMARY OF THE INVENTION

The present invention provides for a process and a product produces a solid light-condensing fiber with a point attachment and having a distal end possessing a fine texture, and a high aspect ratio cone surface that provides for optical fiber blood glucose monitoring with small blood samples.

The textured distal end of the solid light-conducting fiber has a non-contiguous protective coating first deposited thereon and relatively uniformly distributed across the textured surface. The protective coating is further treated by being placed in a vacuum and then subjected to direct hyperthermal beams comprising oxygen ions or atoms.

BRIEF DESCRIPTION OF THE DRAWINGS

FIG. 5 is a composed of FIGS. 5(A) and 5(B), wherein

DETAILED DESCRIPTION OF THE PREFERRED EMBODIMENTS

Figure 1:
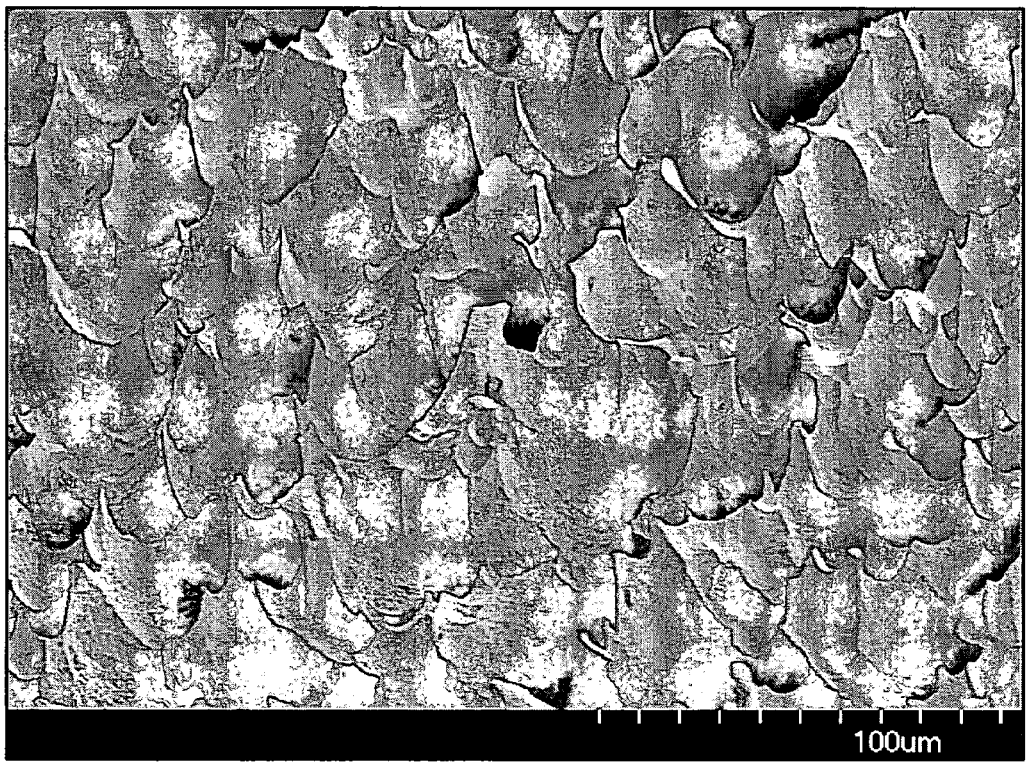
FIG. 1 illustrates a prior art Scanning Electron Microscope image of the end of an optical fiber that was textured by the use of thermal energy (<0.5 eV) atomic oxygen through salt dust to enhance texturing.

One of the purposes of the present invention is to create a surface on optically transparent polymers which has closely spaced cones or pillars so as to prevent blood cellular components during optical monitoring from entering the valleys between the cones or pillars, which would otherwise interfere with the optical sensing of blood glucose concentration. It is also a purpose of the present invention to produce a high surface area of high aspect—ratio cones or pillars which are taller than they are wide so as to enable glucose sensing with a minimum volume of blood. The cellular components in blood predominantly consist of red blood cells (erythrocytes of 6.6-7.5 microns diameter) and white blood cells (leukocytes such lymphocytes of 8-10 microns diameter, neutrophils of 12-15 microns diameter, eosinophils of 12-15 microns diameter, basophils of 9-10 microns diameter and monocytes of 16-20 microns diameter). Thus, a 5 micron average spacing between cones or pillars would serve to prevent the cellular components of blood from entering the valleys between the cones and pillars which needs to be occupied by the plasma only so as to prevent optical obstruction of the glucose sensing by light emitted from the sides of the cones on the textured optical fiber end in a manner to be described hereinafter. A further enhancement is provided by having the spacing between cones or pillars be about 1 micron. A high aspect ratio of the texture (cone height to cone separation) provides a greater surface area, thus enabling a smaller volume blood needed to measure glucose concentration.

Another purpose of the present invention is to provide optically transparent polymer fibers that can be successfully utilized for blood sampling. The previously mentioned '737B1 patent disadvantageously comprises a bundle of multiple fibers whose overall diameter could range from 1 to 50 microns in diameter, which is far too small to be practical for blood sampling. More particularly, the fibers need to be able to be held in individual fingers so as to be inserted into a readout device, to be further described hereinafter, after touching to a small spot of blood. Even the largest bundle of 50 microns disclosed in the '737B1 patent is smaller in diameter than an average human hair. Thus, use of such fibers disclosed in the '737B1 patent would cause one to easily break them as well as potentially breading them off (potentially into your skin) when trying to pick up a blood sample on your body. The present invention provides optical fibers that do not suffer the drawbacks of prior art devices.

A still further purpose of the present invention is to provide optically transparent polymer fibers having a desired shape so as to be utilized for blood sampling. The shape of the fibers of '737B1 patent is approximately hemispherical and the fibers are very rounded at their distal ends. This shape is not useful for optical fibers that monitor glucose level. The reason for this undesired shape is that the purpose of the texture on the end of the fibers is to hold the cellular components of the blood from being in contact with the glucose sensing sides of the cones that are interrogated by light beams. However, hemispheres allow a large area of contact between the blood cells and the surfaces of the hemispheres. This large contact area may cause a misinterpretation of the glucose level in the blood because of the light interacting with the blood cells that lie on the surface. As will be further described hereinafter, the present invention provides optical fibers having conical surface structures wherein negligible light reaches the very tip of the cones and such interactions have little impact because of the microscopic contact area. The invention may be further described with reference to the prior art shown in FIG. 2.

Figure 2:
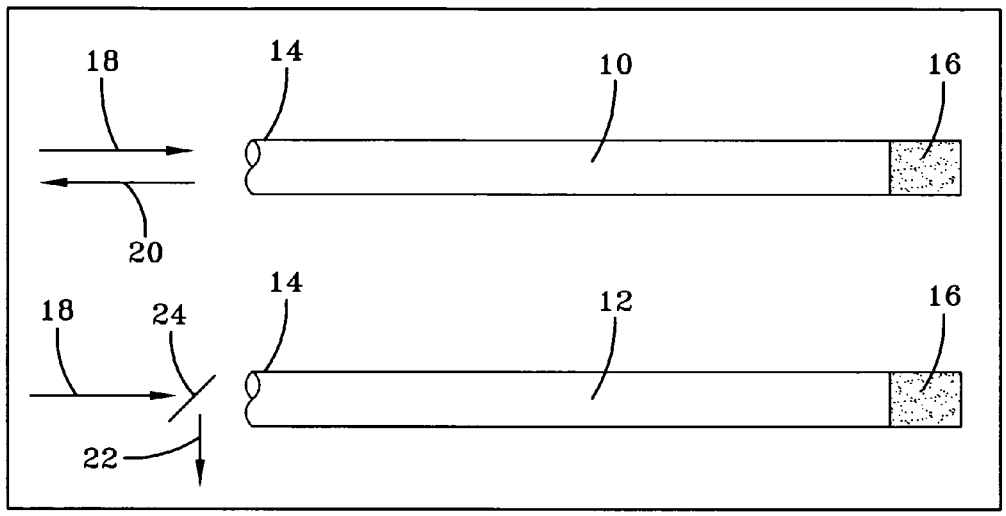
FIG. 2 is a prior art schematic view of fibers with textured surface sites.

FIG. 2 illustrates two solid light-conducting fibers 10, and 12 each being transparent, each having a point of attachment 14, and each preferably comprised of a polymer material, except for silicone. In one embodiment, the fibers 10 and 12 may be comprised of polymethylmethacralate. Each of the fibers 10, and 12 has a textured surface 16 at the distal end thereof that is provided by one of the processes of the present invention to be further described hereinafter with reference to FIGS. 6-9.

In one application, at least one end, that is point of attachment 14, of the light-conductive fibers 10, and 12, is placed adjacent to a light source (not shown) for sending a beam of light 18 down the fiber length. The point of attachment 14 of each of the fibers 10 and 12 is also located adjacent to a device for measuring light beam characteristics of light 20 or 22 emanating from the fibers 10 or 12, respectively, after being reflected by the distal end 16. For fiber 12, a device 24 may be employed to intercept the returning light beam 22 and reflect the light beam 22 downward, as shown in FIG. 2. When the point of attachment 14 is to be adjacent to both the light source and the device for measuring the light beam characteristics, light measurement is dependent upon reflection of the light beam, such as light beam 22, by device 24 as shown for fiber 14.

The textured surface 16 may be treated, so as to contain an analyte responsive reagent (not shown in FIG. 1). A chemiluminescent or fluorescent reaction at the textured site 16 resulting from reagent-analyte interactions can be advantageously utilized wherein a portion of the chemiluminescent or fluorescent light enters the fiber 10 or 12, for detection and quantitation. The textured surfaces 16 may be further described with reference to prior art shown in FIG. 3.

Figure 3:
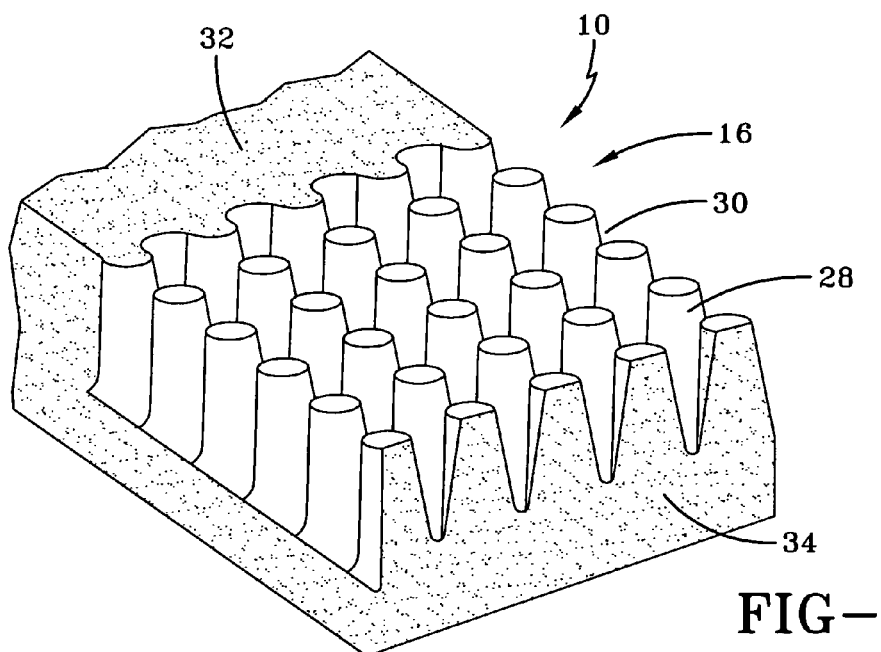
FIG. 3 is a prior art schematic view of a cone field within a textured surface of an optic fiber.

FIG. 3 provides an enlarged view of a cutaway section of a fiber 10 having a textured surface 16. A textured surface 16 is schematically depicted in this case as an array of cone-shaped projections or pillars 28 defining a cone field 30, which has been formed within the surface 32 of a fiber by removal of portions of surface 32 and subsurface 34 material. Further details of the textured surface 16 may be further described with reference to prior art in FIG. 4.

Figure 4:
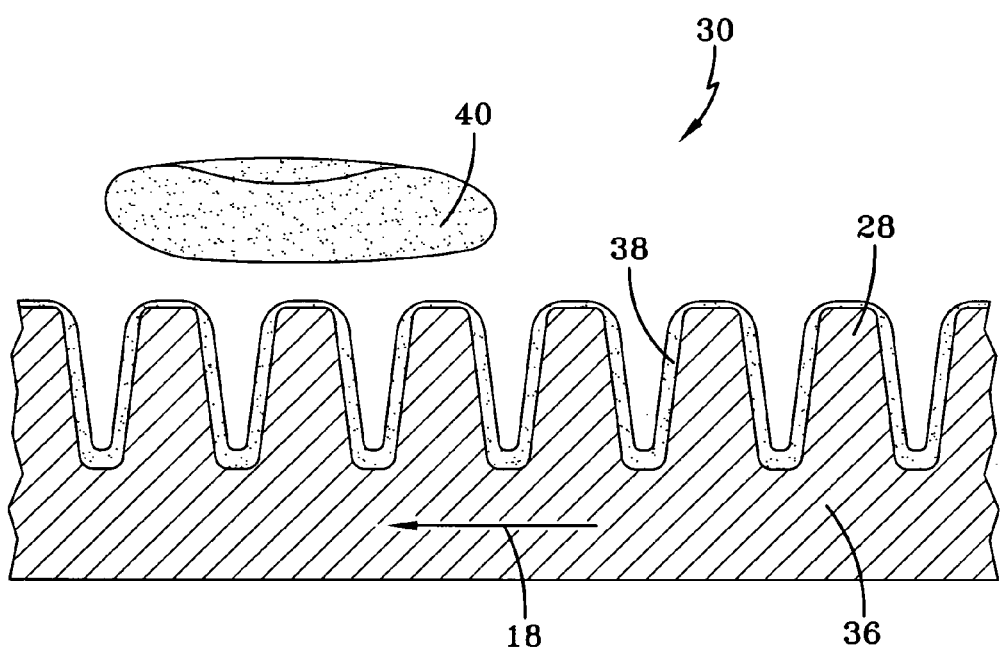
FIG. 4 is a prior art cross-section of a cone field with the deposited reagent, along with adjacent erythrocyte.

FIG. 4 shows a representative cross-section 36 of the cone field 30, wherein a deposit 38 of the analyte-responsive reagent has been conveniently placed within the crevices between cone projections 28. Also shown in FIG. 4, is a representation of an erythrocyte 40 (a red blood cell), whose size in relationship to the openings between the cones of the cone field is large, such that it can typically make no more than incidental contact with the outermost projections of the cones 28. In a determination of a small analyte, such as glucose, the reagent deposit 38 within the cone field 30 is readily accessed by the analyte, but protected from the erythrocytes 40 based on size selection by the cone field pattern. Changes in the reagent deposit 38, such as by development of a colored complex through reaction with an analyte, is advantageously detected by means of a light beam (indicated by the arrow 18) being transmitted through the matrix of the fiber. The textured surface 16 is generally in the form of conical or ridge-like structure microns high and wide having a desired aspect ratio (length/wide) which is preferably greater than one (1). The term "cone field" is herein defined to include textures, which are not necessarily in the specific shape of cones, but may include various linear, box-like or angular arrays of projections so long as their aspect ratio is greater than one (1).

The analytic-responsive reagent placed between the crevices of the cones or pillars 28 may be one of many analyte-sensing systems. In a manner known in the art, for blood glucose determinations, the analyte-sensing system is preferably a composition including a peroxidase enzyme and color-generating chemical couplers. Many combinations of such chemical systems for blood glucose determinations are disclosed and described in U.S. Pat. No. 4,935,346, which is herein incorporated by reference. For antigens, antibodies, enzymes, enzyme inhibitors, and various other biochemical agents, attachment of affinity ligands to the textured surface 16 may be practiced. Herein, the light traveling through the fiber is affected by the development of resulting affinity complexes on the textured fiber surface 16. Alternatively, chemiluminescent or fluorescent techniques may be utilized to highlight the affinity attachment of specific biomolecules on the textured surface, a portion of the chemiluminescent or fluorescent light being captured and transmitted through the fiber to a detector. Attachment of ligands to polymeric surfaces through covalent binding is well known in the art of affinity membranes.

In a preferred method of use of the invention, a light-conducting fiber, such as 10 of FIG. 2, having a textured site 16 thereon is located at attachment point 14 adjacent to a light source for transmittal of a light beam 18 into the fiber 10, and adjacent also to a device for analysis of light beam characteristics of light beam 20 emanating from an opposite end of the fiber 10 after it is reflected by the textured site 16. In a most preferred embodiment, both light input and emanation thereof are at one end of a fiber 10 of predetermined length, and the textured site 16 is at an opposite end of the fiber 10. The textured surface site 16 is first impregnated with an analyte responsive reagent, such as a plasma coated analyte. The textured site 16, is then wetted with a fluid, such as by contacting the fiber at this site with a small droplet of blood. Interaction of the reagent with the analyte, if any, present in the fluid is allowed to occur, resulting in an observable physical or chemical change at the textured site 16. Light passing through the fiber 10 in the region of the textured site 16 is altered in its characteristics such as frequency and amplitude, one or more of these changes being detectable and preferably quantifiable by the device utilized for analysis of light beam 20 emanating from the fiber. More particularly, light intercepting the textured surface 16 creates a change in the spectral reflectance as a result of the light interacting with the plasma-coated analyte surface 16.

As previously mentioned, the diameter of the optical fibers 10 and 12 is important to the practice of the present invention and it is preferred to be in the range of about 1.0 mm to about 2.0 mm. This diameter provides a fiber 10 or 12 that is able to be held in the fingers of an individual, so as to be placed in the line of sight of the device utilizing the light beam 20 after the textured surface 16 touches a small spot of blood. Without the benefits of the present invention, the usage of prior art fibers having typical diameters from 1 to 50 microns corresponding to the diameter of an average human hair may very likely cause the easy breakage of the prior art fiber in use, as well as potentially breaking the fibers off (possibly into the skin) when trying to pick-up a blood sample from the individual for blood glucose monitoring.

As also previously mentioned, the shape of cones of the textured surface 16 of the fibers 10 and 12 that come into contact with the blood being sampled is important to the practice of the present invention and is preferably conical. The reason for the desired conical shape is that the purpose of the texture, such as textured surface 16, on the end of the fibers, such as 10 and 12, is to hold the cellular components of the blood from coming in contact with the glucose sensing sides of the cones that are interrogated by light beams. If shapes other than round, such as hemispheres, were used these shapes would allow a large area of contact between the blood cells and the surfaces of the hemispheres. This large contact area may cause a misinterpretation of the glucose level in the blood because of the light beam 20 interacting with the blood cells that lie on the surface. However, for conical surface structures, as provided by the present invention, negligible light reaches the very tip of the cones 36 and such interactions have little impact because of the microscopic contact area therebetween.

As known in the art, a diabetic patient wishing to measure his or her blood glucose level would pierce the skin of a finger with a lancet whose size and depth of penetration is designed to provide a minimally sized droplet, to be further described hereinafter, of blood at a minimized level of associated pain. The patient would preferably then touch a textured site 16 to the droplet, the fiber being advantageously pre-fixed to a measurement device. The patient would then read and record his or her blood glucose concentration determined upon wetout of the textured surface site 16 by the minimally sized blood droplet. The minimally sized droplet is to be further described hereinafter. The preparation of the textured surface 16 is of particular importance to the present invention and will be further described hereinafter with reference to FIGS. 5-8.

One of the main contributions of the present invention is to provide a method of producing cones 28 and pillars, for one embodiment, on polymethylmethacralate (PMMA) optical fibers 10 and 12 used for glucose monitoring. In general, and as will be more fully described hereinafter, the method comprises using electron beam evaporation to deposit a non-contiguous protective film on the distal ends 16 of the PMMA fibers 10 and 12 and does not suffer the drawbacks of photolithograph discussed herein in the "Background" section. The partial coverage of protective coating on the fibers is randomly, but rather uniformly distributed across the end of the optical fibers 10 and 12. After the protective coating deposition, the distal ends 16 of the fibers 10 and 12 are then exposed to hyperthermal atomic oxygen, which oxidizes the areas that are not protected by the protective coating. The resulting PMMA fibers 10 and 12 have a greatly increased surface area and the cones 28 or pillars are sufficiently close together that the cellular components, such as those shown in FIG. 4, in blood are excluded from passing into the valleys between the cones 28 and pillars. The optical fibers 10 and 12 are then coated with appropriated surface chemistry so that the optical fibers 10 and 12 can optically sense the glucose level in the blood sample, while requiring a much smaller blood sample than that with conventional glucose monitoring.

The method used to produce closely-spaced high-aspect ratio cones or pillars 28 in optically clear polymers, such as PMMA, comprises applying a protective film to the distal end 16 of the optical fibers 10 and 12. This can be done relatively quickly (seconds to a few minutes) by a process selected from the group comprising electron beam evaporation, ion beam sputtering, RF sputtering, and thermal evaporation, all known in the art.

The protective coating preferably comprises aluminum, but other protective coatings can be applied which simply have the properties that prevent atomic oxygen from oxidatively eroding them. Other materials may comprise metals (gold), metal oxides (silicon dioxide), and soluable salts (sodium chloride). In one embodiment, the protective film comprises aluminum having a thickness in the range from about 10 microns to about 500 microns.

Figure 5A:
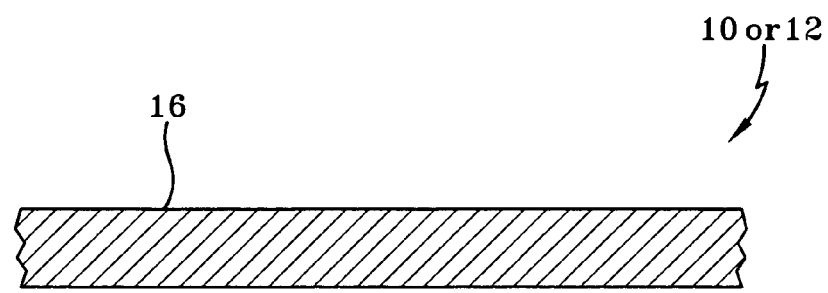
FIG. 5(A) is a side section view of the initial acrylic optical fiber surface used in the practice of the present invention.
Figure 5B:
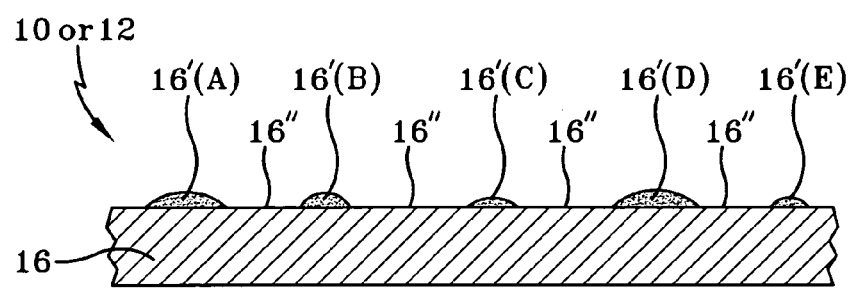
FIG. 5(B) is a side section view of the initial acrylic optical fiber surface of FIG. 5(A) after vapor deposition of aluminum serving as the protective coating of the present invention.

The deposition of the protective film may be further described with reference to FIG. 5. FIG. 5 is composed of FIGS. 5(A) and 5(B), wherein FIG. 5(A) is a side section view of the initial surface 16 of an acrylic optical fiber, such as 10 or 12, used in the practice of the present invention, and FIG. 5(B) is a side section view of the initial surface 16 of the acrylic optical fiber 10 or 12 of FIG. 5(A) after vapor deposition of aluminum serving as the protective coating of the present invention. FIG. 5 generally illustrates a portion of protective film with the reference designation 16' and shown as being distributed across a portion of the distal end 16. The protective film 16' is comprised of islands shown in part with reference designations 16' (A), 16' (B), 16' (C), 16' (D) and 16' (E) with 16' (A) and 16' (D) being large islands relative to the smaller islands 16' (B), 16' (C) and 16' (E). As will be further described with reference to FIG. 8, that after the coating 16' is deposited and hyperthermal atomic oxygen is used to etch the unprotected areas of the acrylic fibers, the aluminum thin protection islands 16' (A) . . . 16' (E) are also gradually eroded away because an end Hall ion source produces oxygen ions with energies above the sputter threshold of aluminum. This means that the small aluminum islands disappear, such as 16' (B), 16' (C) and 16' (E) leaving sharp pointed structures and the large islands, such as 16' (A) and 16' (D) are made smaller in diameter and thickness thus forming a cap thereon.

It is preferred that the vapor provided by the process selected to deposit the protective film 16', such as electron beam evaporation, be thin enough to cause the protective film 16' to nucleate into islands, such as 16' (A) . . . 16' (E), with uncoated regions 16" between each island 16' (A) . . . 16' (E). This allows regions where atomic oxygen is applied to be protected from the PMMA by the islands 16' (A) . . . 16' (E) and regions, such as those of 16", where the PMMA is exposed, so as to be able to be oxidized by atomic oxygen. Each exposed region, such as those of 16", have surfaces comprised of exposed polymers that are textured by a directed beam of energetic atomic oxygen atoms or ions. The directed beam of energetic atomic oxygen may be further described with reference to FIGS. 6-8.

Figure 6:
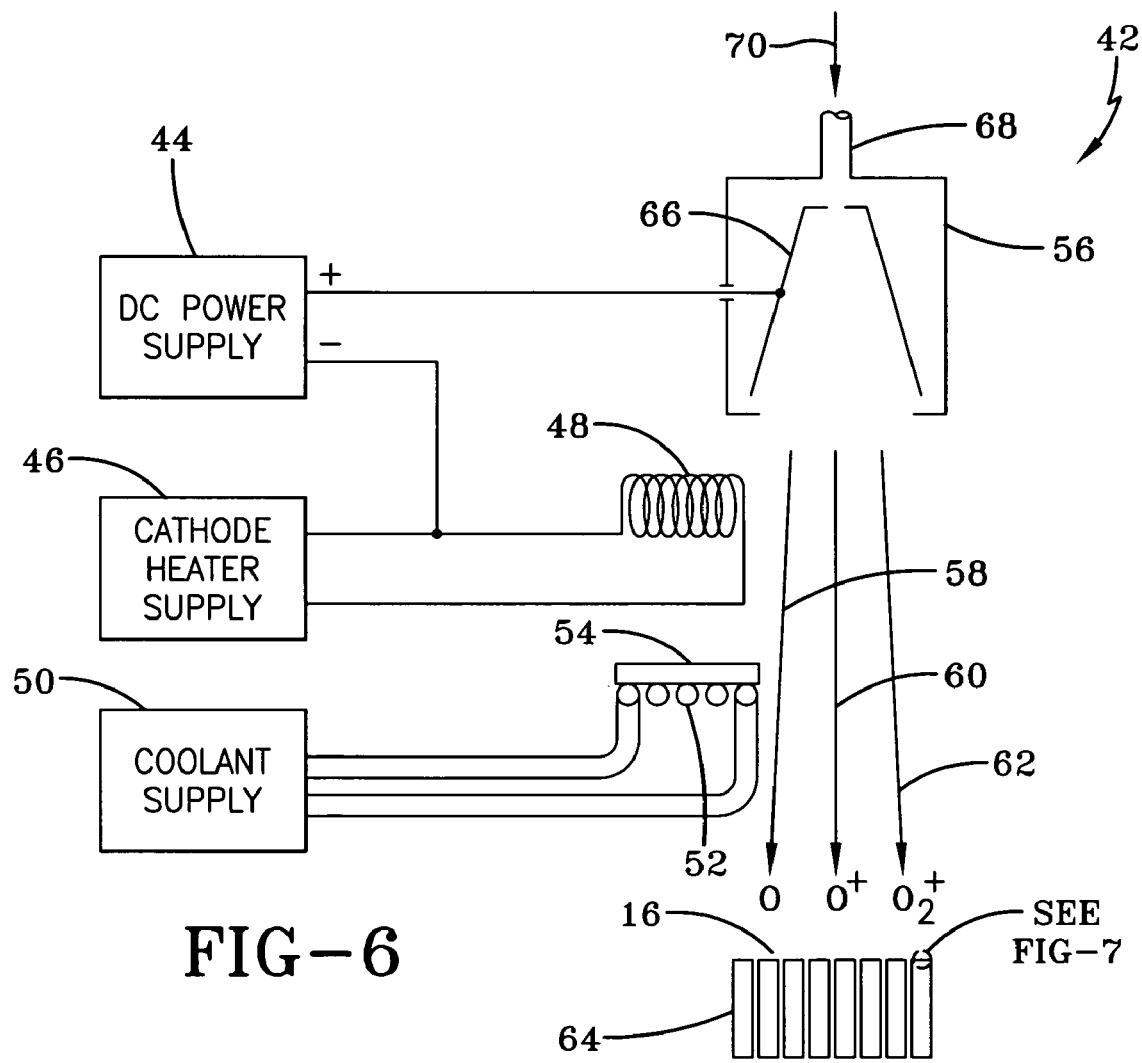
FIG. 6 is a block diagram of a process that provides hypothermal ionic or atomic oxygen texturing of optical surfaces.
Figure 8:
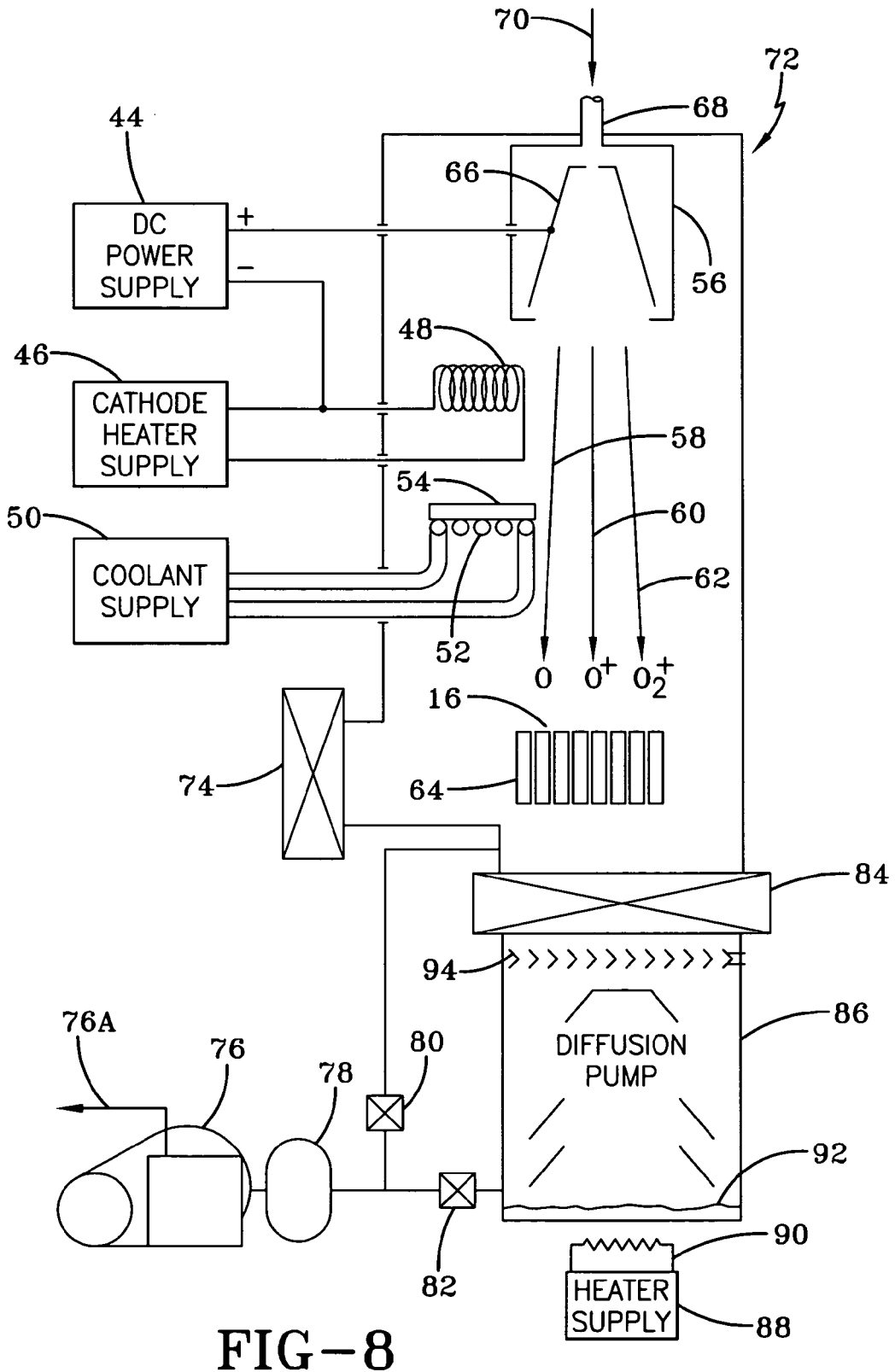
FIG. 8 is a block diagram of the apparatus that provides the desired process of the present invention.
Figure 9:
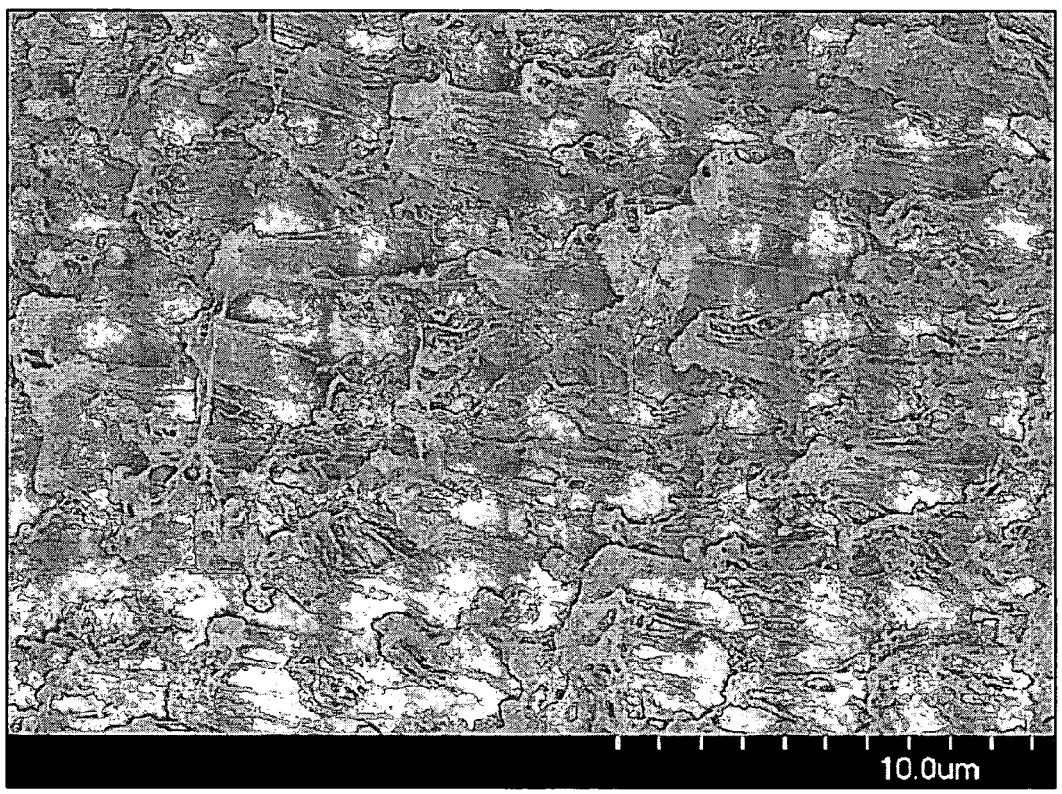
FIG. 9 is a Scanning Electron Microscope image of an atomic oxygen textured polymethylmethacrylate optical fiber that was first coated with aluminum and then textured by means of an End Hall atomic or ionic oxygen source which produces hyperthermal (<1 eV) atomic oxygen ions.

In general, the arrangements shown in FIGS. 6 and 8 provide one or more processes used to produce closely—spaced high aspect-ratio cones or pillars 28, as shown in FIG. 9, to be further described hereinafter, in optically clear polymers consisting of exposing the surfaces of the polymers, already having the non-contiguous protective coating 16' deposited thereon, to be textured by a directed beam of energetic atomic oxygen atoms or ions. The energy of the atomic oxygen atoms or ions should be hyperthermal (>1 eV) so as to produce the textured surfaces shown in FIG. 9.

In the practice of the present invention, it was determined that the energy level desired was greater than 1 eV. It was further determined that the preferred range was energies in the range of about 30 eV to about 150 eV. So although it is desired to use energy levels of greater than 1 eV, the typical range of energies used to actually do the texturing, which work best in terms of high length-to-width cones 28, is in the 30 eV to 150 eV range.

The reactions, provided by the present invention, produce closely-spaced high aspect-ration cones or pillars. To perform this process, one must place the optical polymers, already having the non-contiguous protective coating 16' deposited thereon, to be textured in a vacuum system, which evacuated to $\leq 1 \times 10^{-5}$ torr. Without the vacuum system atomic and ionic oxygen may be attenuated such as that which occurs at high pressure, such as air pressure. An energetic (>1 eV) beam of atomic oxygen atoms or ions is then formed in the vacuum system by ion or atom beam accelerating devices, such as End Hall ion accelerators, electron bombardment ion thrusters or other electrostatic, electromagnetic or arc devices, to be further described hereinafter. These different sources need to be able to produce oxygen ion or atom energies of greater than 1 eV.

As known in the art, the resulting beams developed from the source of greater than 1 eV are directed hyperthermal beams. In one embodiment, the ends of a thousand optical fibers, already having the non-contiguous protective coating deposited thereon, can be treated at one time. An arrangement 42 of the apparatus for the desired processes is shown in FIG. 6, which is devoid, for the sake of clarity, of the desired vacuum source, which will be further described hereinafter with reference to FIG. 8.

The arrangement 42 of FIG. 6 comprises a DC power supply 44 having a preferred range of 25-150 volts, a cathode heater supply 46 connected to a cathode 48, and a cooling supply 50 preferably being of water and connected to a water cooling coil 52 arranged with a water-cooled radiation shield 54.

The arrangement 42 further comprises a hyperthermal atomic oxygen source 56 that can be any source of oxygen atoms or ions that produce a directed beam of energy greater than 1 eV and shown as beams 58, 60, or 62 and indicated as 0, $0^+$, $0_2^+$ respectively. The ions in the beams 58, 60, and 62 can be single or multiply charged. The ion or atomic source 56 can be an End Hall source, an electron bombardment ion source, a DC plasma source, a microwave plasma source or any other source provided the source delivers a hyperthermal beam of greater than 1.0V comprised of oxygen atoms or ions.

The positive terminal of the DC power supply 44 is connected to an anode 66 of the source 56, whereas the negative terminal of the DC power supply 44 is connected to the cathode 48. The directed hyperthermal beams 58, 60, and 62 are preferably directed from one direction onto the distal end 16 of each of the light-conducting fibers of the bundle 64, so as to produce the textured surface 16 thereon. The protective coated regions, such as those coated with the protective film 16' as shown in FIG. 5, cause the spacing between the cones or pillars 28 to be greater than the natural texture of the fibers 10 and 20, wherein natural texture is the more closely spaced texture that results from directed atomic oxygen reactive etching and/or sputter erosion of a polymer. Surfaces become microscopically rough as they are eroded by directed beams which is a direct result of statistical erosion processes, known in the art. If the spacing was not greater than the natural texture, then features of the cones 28 would often undesirably be too narrow for optimal light propagation into the cones 28. The textured surface 16 may be further described with reference to FIG. 7.

Figure 7:
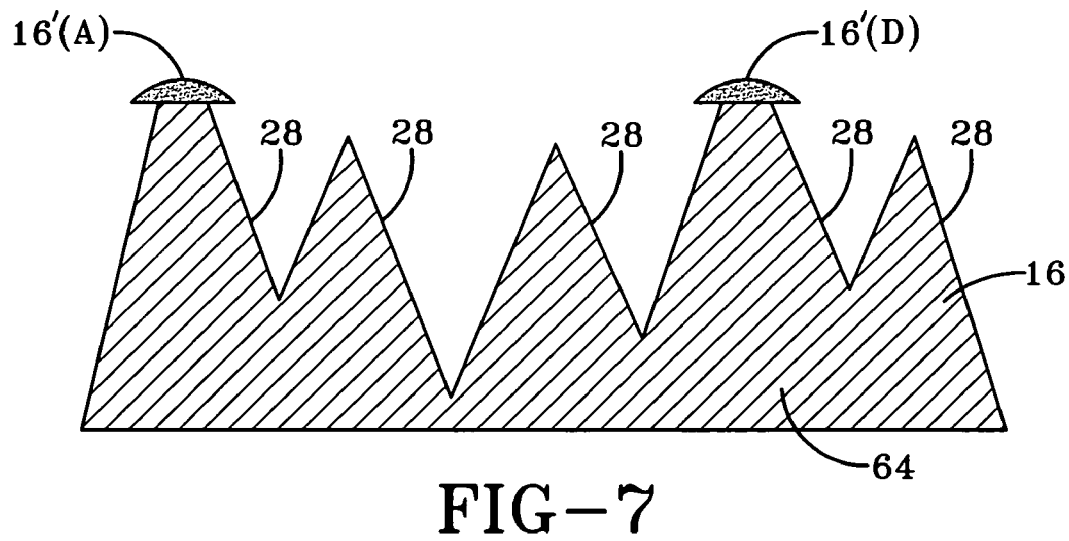
FIG. 7 is a side section view of initial acrylic optical fiber surface of FIG. 5(A) after vapor deposition of the protective coating and atomic oxygen etching.

FIG. 7 shows the textured surface 16 as comprising the cones 28 that are separated from each other by distance no less than 1 micron and have an aspect ratio (length/width) that is in the range of about 1 to about 6. As previously mentioned, after the coating 16' is deposited and hyperthermal atomic oxygen is used to etch the unprotected areas of the acrylic fibers 10 or 12, the aluminum thin protection islands 16' (A) . . . 16' (E) are also gradually eroded away because the end Hall ion source 56 produces oxygen ions with energies above the sputter threshold of aluminum. This means that the small aluminum islands 16' (B), 16' (C) and 16' (E) (shown in FIG. 5(B)) disappear, leaving sharp pointed structures as shown in FIG. 7, and the large islands 16' (A) and 16' (D) (shown in FIG. 5(B)) are made smaller in diameter and thickness thus forming a cap. The end Hall ion source 56 produces ions in the 30 to 150 eV range at an average of 70 eV, and the sputter threshold (the energy above which ions have enough energy to cause sputter erosion) for aluminum and aluminum oxide is in the 10 to 30 eV range. Thus, the thin film islands, such as 16' (B), 16' (C) and 16' (E) (shown in FIG. 5(B)) gradually sputter away, such that the small flat top structures will turn into conical structures and the larger aluminum protective islands, such as 16' (A) and 16' (D) get smaller and thinner and result in the flat topped structures that can be seen occasionally in the scanning electron microscope image along with lots of the smaller pointed structures.

The distance between the source 56 of FIG. 6 and the bundle 64 of optical fiber can be varied from 3 cm to 200 cm provided the atom or ion beam 58, 60, and 62 does not become depleted by scattering, in a manner known in the art, from background oxygen gas molecules in a vacuum chamber, to be further described hereinafter with reference to FIG. 8. The thermal shield 54 is used to prevent sensitive optical fibers, such as those comprised in bundle 64, from melting. The shield 54 may be a water-cooled shield or may comprise a multi-layer insulation or even eliminated if the End Hall source 56 uses a hollow cathode and does not produce much thermal radiation. For such an arrangement, the optical fibers do not need to be relatively close to the End Hall source 56, and if the optical fibers are farther away there is less cooling needed thereof.

The bundle 64 is preferably brought together so as to provide a hexagonal close-packed array so that the directed atomic oxygen or ion beam 58, 60, or 62 impinges on the end surface of all the fibers at once so as to produce the textured surface 16 of all of the fibers making up the bundle 64. The atomic oxygen source 56 may cause heating of the optical bundle 64. To prevent the heat sensitive polymers, such as polymethylmethacrylat from melting, the water cooled or thermal-shield chill 54 is inserted between the End Hall cathode 66 and the optical fiber bundle 64 as shown in FIG. 6.

In general, the length of the cones 28 and the spacing between the cones 28, can be varied by simply changing the fluence (atomic and ionic oxygen exposure level). The length and height have been found to grow in proportion to the square root of the fluence (known in the art). The vacuum source in which the bundle 64 of solid light-conducting fibers are placed before being subjected to the hyperthermal beams 58, 60, or 62, may be further described with reference to FIG. 8.

FIG. 8 shows a vacuum source 72 having a door 74 through which the bundle 64 of fibers may be entered. The vacuum source 72 can be any configuration that allows evacuation down to a pressure of less than $1 \times 10^{-5}$ torr during atomic oxygen operation.

The vacuum source 72 shows provisions of a roughing pump 76 that provides an output to a blower pump 78 which, in turn, provides an output source of air to valves 80 and 82, all in a manner known in the art. The valve 80 directs its output into the vacuum source 72 by way of gate valve 84, whereas the valve 82 directs its output into a diffusion pump 86 (also known in the art).

The diffusion pump 86 receives heat from a heat supply 88 by way of elements 90 and 92. The diffusion pump 86 also receives cooling ($LN_2$) by means of a liquid nitrogen cooled trap 94.

The apparatus of FIG. 8, using conventional elements, provides for one method of the present invention that causes a solid light-conducting fiber used in the analyses of blood and to have a desired textured surface 16 by first placing the solid light-conducting fibers 10 or 12 having the distal end 16 in a vacuum source 72 and then subjecting the distal end 16 to directed hyperthermal beams 58, 60, or 62 comprising oxygen atoms or ions. The operation of the apparatus of FIG. 8 provides for textured surface 16, which may be further described with reference to FIG. 9.

FIG. 9 shows a Scanning Electron Microscope image of an atomic oxygen textured polymethylmethacrylate optical fiber that first had a non-contiguous protective coating 16' deposited on its distal end 16. The distal end 16 having the protective coating 16' was then textured by the practice of the present invention by using a hyperthermal (>1 eV) End Hall atomic or ionic oxygen source provided by the apparatus of FIG. 8. FIG. 9 shows that the separation between pillars and cones is $\leq 1$ micron and extremely thus suitable to prevent the cellular components 40 of blood, such as that shown in FIG. 4, from entering the valleys between the cones or pillars 28 as shown in FIG. 4. In addition, the aspect ratio of the fibers is much greater than 1, far better than the aspect ratio of less than one (1) achieved by the thermal energy atomic oxygen texturing shown in FIG. 1.

One of the primary advantage of the present invention, relating to its minimally invasive feature, is the presence of a large surface area in a very small, localized area, by which a greatly increased level of analyte-responsive reagent can be deposited and maintained. As more fully described in the previously incorporated by reference '937 patent, the large surface area disclosed in the '937 patent allows for the accommodation of blood samples preferably in the range of 1.0 to 2.5 microliters. Based on the practice of the present invention, a ratio of 2 to about 6 increase in effective area relative to the teaching of the '937 patent is achieved which, in turn, decreases the amount of blood sample required by a factor of 2 to about 6. Thus, the practice of the present invention accommodates a blood sample in the range from about 0.5 to 1.25 microliters to about from 0.16 to about 0.41.

It should now be appreciated that the practice of the present invention first places a places a protective coating of the distal end of an optical fiber and then uses directed hyperthermal equal or greater than 1 eV beams comprising oxygen atoms or ions to produce textured surfaces 16. The present invention also provides for the thermal radiation shielding to prevent overheating of the textured surfaces, while at the same time, one embodiment uses an End Hall atomic or ionic oxygen source, having a hollow cathode, and providing for texturing optical polymer surfaces without the use of thermal shielding.

The present invention makes use of the natural formation of cones or pillars that result when the distal end of an optical fiber has a protective coating deposited thereon and then the distal end is subjected to direct hyperthermal (greater than 1 eV) atomic or ionic oxidation. The apparatus of the present invention allows these cones or pillars 28 to be sufficiently close or spaced, so as to prevent cellular blood components from interfering with optical sensing of blood glucose concentration. The present invention also provides for small samples of blood to be used as compared to the previous prior art sensors performing the same task.

While the present invention has been described more particularly in the context of glucose determinations and whole blood by diabetics, the invention may be utilized in the determination of other analytes as well, or as even simultaneous determination of two or more analytes.

While the preferred invention is presently contemplated that has been shown in the drawing as described herein, variations of preferred embodiments will be apparent to those skilled in the art and the invention should not be construed as limited to the specific forms as shown and described herein, but rather set forth in the following claims.

What I claim is:

1. A sensor comprising a single solid light-conducting fiber having a textured surface site consisting of a textured distal end first having a non-contiguous protective coating deposited thereon which is treated by being placed in a vacuum and then subject to directed hyperthermal beams comprising oxygen ions or atoms, wherein said textured distal end comprises said non-contiguous protective coating thereon and cones separated from each other by an amount which is about 1 micron.

2. The sensor according to claim 1, wherein said protecting coating is of a material selected from the group comprising aluminum, gold, silicon dioxide and sodium chloride.

3. The sensor according to claim 2, wherein said aluminum has a thickness in the range from about 10 microns to about 500 microns.

4. The sensor according to claim 1, wherein said single solid light-conducting fiber has a diameter in the range from about 1.0 mm to about 2.0 mm.

5. The sensor according to claim 1, wherein said textured distal end comprises cones having a length to width ratio, which is greater than one.

6. The sensor according to claim 5, wherein said cones have a conical shape.

7. The sensor according to claim 1, wherein an analyte-responsive reagent is deposited on said fiber at said textured surface site.

8. The sensor according to claim 1, wherein said light-conducting fiber is transparent and is of polymer material except for silicone.

9. The sensor according to claim 8, wherein said light-conducting fiber is polymethylmethacralate.

10. A method of producing a solid light-conducting fiber used in the analysis of a blood comprising the steps of:
 a) selecting at least one single solid light-conducting fiber having a point of attachment and a distal end;
 b) depositing a protective coating on said distal end of said at least one light-conducting fiber;
 c) placing said at least one light-conducting fiber having said protective coating on said distal end in a vacuum source; and
 d) subjecting said distal end to directed hyperthermal beams comprising oxygen ions or atoms.

11. The method according to claim 10, wherein said protective coating is of a material selected from the group comprising aluminum, gold, silicon dioxide, and sodium chloride.

12. The method according to claim 11, wherein said aluminum has a thickness in the range from about 10 microns to about 500 microns.

13. The method according to claim 10, wherein said single light-conducting fiber is polymethylmethacralate.

14. The method according to claim 10, wherein said single solid light-conducting fiber has a diameter in the range from about 1.0 mm to about 2.0 mm.

15. The method according to claim 10, wherein said vacuum source supplies a pressure of less than about $1 \times 10^{-5}$ while said distal end is being subjected to said directed hyperthermal beams comprising ions or atoms.

16. The method according to claim 10, wherein said directed hyperthermal beams have an energy level that is in the range from about greater than 1 eV to about 100 eV.

17. The method according to claim 16, wherein said directed hyperthermal beams is in the range from about 30 eV to about 150 eV.

18. The method according to claim 10, wherein said directed hyperthermal beams comprising oxygen ions or atoms are provided from a source selected from the group consisting of an End Hall source, an electron bombardment ion source, a microwave plasma source and an arc source.

19. The method according to claim 18, wherein said selected source and said distal end are spaced apart from each other by a distance in the range from about 3 cm to about 200 cm.

20. The method according to claim 19, wherein said at least one solid light-conducting fiber comprises a plurality arranged in a bundle and each having a distal end.

21. The method according to claim 20, wherein said selected source and said bundle has a shield interposed therebetween and wherein said selected source and said distal ends of said bundle are spaced apart from each other by a distance in the range from about 3 cm to about 200 cm.

22. The method according to claim 21, wherein said shield is selected from the group consisting of a water-cooled shield and multilayer insulation shield.

23. The method according to claim 18, wherein said source is an End Hall source having a hollow cathode and separated from said distal ends of said bundle by a distance in the range from about 3 cm to about 200 cm.

24. A method of analyzing for an analyte in a fluid comprising the steps of:
 providing a single solid light-conducting fiber with a point of attachment and having a distal end with a protective coating deposited thereon and wherein said protective coating is further prepared by being placed in a vacuum and then subjected to directed hyperthermal beams comprising oxygen ions or atoms, said distal end further having an analyte-responsive reagent deposited thereon;
 bringing a droplet of the fluid containing said analyte and having an initial sampling volume of less than 5 microliters into contact with said distal end of said site, so as to produce a physical or chemical response by interaction of said reagent with said analyte, said response being detectable by a change in characteristics of a light beam;
 transmitting a light beam from a light source into said point of contact and into said distal end; and
 analyzing said light beam reflected from said distal end for said change, said change being correlative with presence of said analyte in the fluid.

25. The method according to claim 24, wherein said change is correlative with the concentration of said analyte in the fluid.

26. The method according to claim 25, wherein the fluid being brought into contact with said fiber has an initial sampling volume of about 0.2 to about 0.4 microliters.

27. The method according to claim 26, wherein the fluid is blood and the analyte is glucose.

* * * * *